(12) United States Patent
Colladant et al.

(10) Patent No.: US 6,548,664 B1
(45) Date of Patent: Apr. 15, 2003

(54) OCTAHYDRO-6, 10-DIOXO-6H-PYRIDAZINO/1,2-A/ /1,2/DIAZEPIN-1-CARBOXYLIC ACID, DERIVATIVES, PREPARATION METHOD AND USE FOR PREPARING THERAPEUTICALLY ACTIVE COMPOUNDS

(75) Inventors: Colette Colladant, Rosny sous Bois (FR); Veronique Cro-cq, Dijon (FR); John Patrick Larkin, Champagne sur Oise (FR); Patrick Roussel, Thiais (FR)

(73) Assignee: Aventis Pharma S.A. (FR)

(*) Notice: Subject to any disclaimer, the term of this patent is extended or adjusted under 35 U.S.C. 154(b) by 0 days.

(21) Appl. No.: 09/674,327

(22) PCT Filed: Apr. 26, 1999

(86) PCT No.: PCT/FR99/00981

§ 371 (c)(1),
(2), (4) Date: Oct. 31, 2000

(87) PCT Pub. No.: WO99/55724

PCT Pub. Date: Nov. 4, 1999

(30) Foreign Application Priority Data

Apr. 27, 1998 (FR) .......................................... 98 05243

(51) Int. Cl.$^7$ .......................................... C07D 487/04
(52) U.S. Cl. .................................................... 540/500
(58) Field of Search .......................... 540/500; 544/224

(56) References Cited

U.S. PATENT DOCUMENTS 4,512,924 A * 4/1985 Attwood et al. ......... 260/243.3
5,656,627 A    8/1997 Bemis et al. ............... 514/221
5,723,602 A * 3/1998 Karanewsky ............... 540/500
6,201,118 B1 * 3/2001 Robidoux et al. .......... 540/500

FOREIGN PATENT DOCUMENTS

| WO | 9323403 | 11/1993 |
| WO | 9533751 | 12/1995 |
| WO | 9722619 | 6/1997 |

OTHER PUBLICATIONS

Attwood et al. {J. Chem. Soc. Perkin Trans. 1, 6, (1986), 1011–1019}.*

* cited by examiner

Primary Examiner—Richard L. Raymond
Assistant Examiner—Kahsay Habte
(74) Attorney, Agent, or Firm—Bierman, Muserlian and Lucas

(57) ABSTRACT

The invention concerns compounds of formula (I) in SR configuration or in the form of a SR+SS mixture, wherein R represents a hydrogen atom, an alkyl or aralkyl radical containing up to 18 carbon atoms, the amine function being free or protected. The compounds can be used for preparing active principles for medicines.

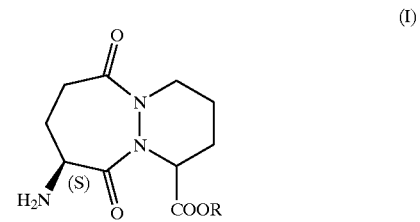

(I)

8 Claims, No Drawings

OCTAHYDRO-6, 10-DIOXO-6H-PYRIDAZINO/1,2-A/ /1,2/DIAZEPIN-1-CARBOXYLIC ACID, DERIVATIVES, PREPARATION METHOD AND USE FOR PREPARING THERAPEUTICALLY ACTIVE COMPOUNDS

This application is a 371 of PCT/FR99/00981 filed on Apr. 26, 1999.

The present invention relates to new derivatives of octahydro-6,10-dioxo-6H-pyridazino[1,2-a][1,2]diazepine-1-carboxylic acid, their preparation process and their use in the preparation of therapeutically active compounds. U.S. Pat. No. 4512924, WO 93 23403, U.S. Pat. No. 5723602, WO 97 22619, U.S. Pat. No. 5,656,627 and WO 33751 describe derivatives of 9-amino-octahydro-6,10-dioxo-6H-pyridazino[1,2-a][1,2]diazepine-1-carboxylic acid, the amine of which is optionally protected in the form of a phthalimido of 1S,9S configuration, as a starting product for the preparation of products as medicaments. Obtaining the SS diastereoisomer is carried out by separation methods, in particular by crystallization or chromatography, in a stage upstream of the cylization.

A subject of the invention is the compounds of formula

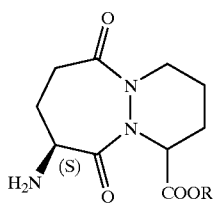

(I)

of SR configuration or in the form of an SR+SS mixture, in which R represents a hydrogen atom, an alkyl or aralkyl radical containing up to 18 carbon atoms, the amine function being able to be free or protected.

R represents for example an H, methyl, ethyl, propyl, isopropyl, n-butyl, isobutyl or tertbutyl radical, or a benzyl or naphthyl radical. When the amine function is protected, the protection can be carried out according to standard methods for the protection of amines.

A particular subject of the invention is the compounds corresponding to formula (IA):

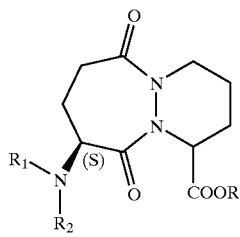

(IA)

of SR configuration or in the form of an SR+SS mixture, in which R retains its previous meaning and either $R_1$ represents

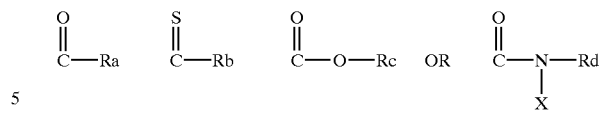

radical

Ra, Rb, Rc and Rd representing an alkyl or aryl radical containing up to 18 carbon atoms, or a mono or polycyclic radical containing one or more heteroatoms, X representing a hydrogen atom, an alkyl radical containing up to 8 carbon atoms or an aryl radical containing up to 14 carbon atoms, and $R_2$ represents a hydrogen atom, or $R_1$ and $R_2$ form together a mono or polycyclic radical containing one or more heteroatoms.

For example, in order to protect the amines, cyclic compounds can be used, for example the

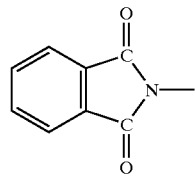

radicals, or also the

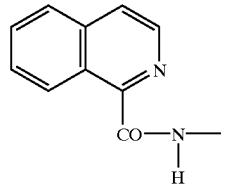

radical.

A more particular subject of the invention is the compounds of formula (IA) in which $R_1$ and $R_2$ together form a polycyclic radical containing one or more heteroatoms and in particular the compounds corresponding to formula $(1A_1)$:

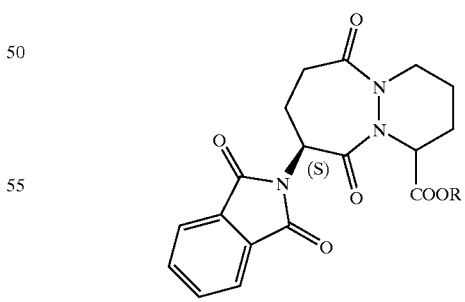

$(IA_1)$ of SR configuration or in the form of an SR+SS mixture.

A particular subject of the invention is the compounds of formula (I) in which R represents a methyl radical, of SR configuration or in the form of an SR+SS mixture.

A subject of the invention is also a process characterized in that a compound of formula (II):

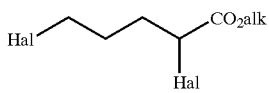

(II)

in which alk represents an alkyl radical containing up to 8 carbon atoms and Hal represents a halogen atom, is subjected to the action of a compound of formula (III):

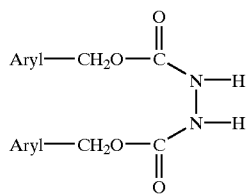

(III)

in which Aryl represents an aryl radical containing up to 14 carbon atoms, in order to obtain the compound of formula (IV):

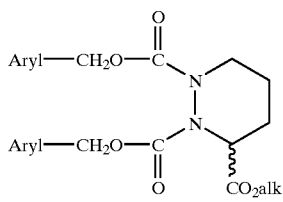

(IV)

which is subjected to the action of a basic agent, in order to obtain the compound of formula (V):

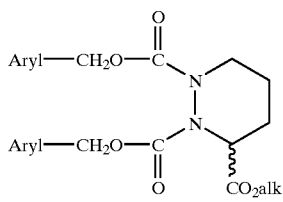

(V)

which is optionally subjected to the action of an alkylation agent in order to obtain the compound of formula (VI):

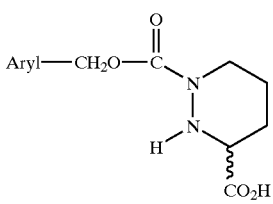

(VI)

which is subjected to the action of a compound of formula VII):

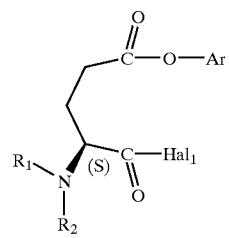

(VII)

in which Hal1 represents a halogen atom and Ar represents an aryl or aralkyl radical containing up to 18 carbon atoms, $R_1$ and $R_2$ retaining the same definition as previously, in order to obtain the compound of formula (VIII):

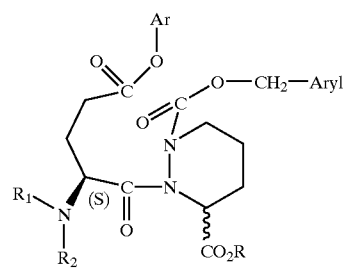

(VIII)

of SR configuration or in the form of an SR+SS mixture, which is subjected to the action of a hydrogenation agent in order to obtain the compound of formula (IX):

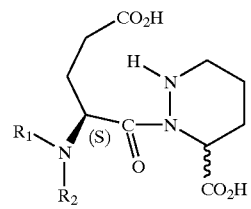

(IX)

of SR configuration or in the form of an SR+SS mixture, which is subjected to the action of a condensation agent in order to obtain the corresponding compound of formula (IA), then if desired, the amine function is released in order to obtain the compound of formula (I) in which the amine function is free.

In a preferred embodiment:
  Hal and $Hal_1$ represent a chlorine atom,
  alk represents an alkyl radical containing up to 4 carbon atoms,
  Aryl represents a phenyl or naphthyl radical,
  aralkyl represents a benzyl radical,
  the reaction between the compounds of formula (II) and formula (III) takes place in the presence of a base for example in the presence of an alkaline carbonate such as potassium carbonate,
  the basic agent which is reacted on the compound of formula (IV) is sodium or potassium hydroxide,
  the alkylation agent which is reacted on the compound of formula (V) is an alcohol for example methanol,
  the condensation between the compounds (VI) and (VII) is carried out in the presence of a base such as pyridine, TEA, diisopropylamine, the hydrogenation agent is for example hydrogen in the presence of palladium on carbon, palladium dihydroxide in the presence of talc, rhodium in the presence of alumina, ruthenium on carbon, or in the presence of Raney nickel, the cyclization is carried out in the presence of $SOCl_2$ or $PCl_5$ or activated esters or in the presence of dehydration agents such as PTSA, the release of the amine can be carried out using hydrazine.

The products (IV), (VII), (VIII) and (IX) used during the process are new products and are in themselves a subject of the present invention.

A more particular subject of the invention is the products the preparation of which is given hereafter in the experimental part and in particular the racemic mixture.

A subject of the invention is also the use characterized in that a compound of formula (I) in the form of an SS,SR mixture, or in SR form, is subjected to the action of a deracemization agent of the asymmetric carbon carried by the ring with 6 members, in order to obtain the compound of formula (Iopt):

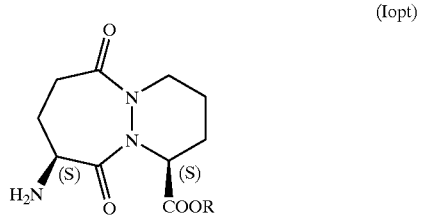

(Iopt)

in SS form, in which the amine function is free or protected and R retains its previous meaning.

A more particular subject of the invention is the use of the compounds of formula (IA) defined above, for the preparation of compounds of formula (IAopt):

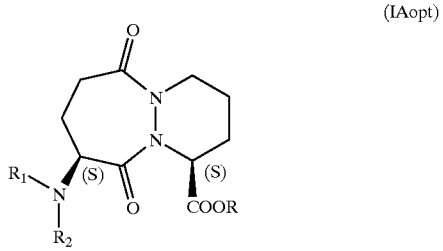

(IAopt)

in the SS form, in which R, $R_1$ and $R_2$ retain their previous meaning.

A more particular subject of the invention is the use characterized in that R represents a methyl radical, and that in which the amine function is protected in the form of phthalimido.

A more particular subject of the invention is the use characterized in that the deracemization agent is a base, more especially a strong base, for example an alkaline or alkaline-earth alcoholate such as sodium or potassium methylate, sodium or potassium terbutylate, or a lithiated amine such as LDA.

A quite particular subject of the invention is the use described hereafter in the experimental part for preparing:

(1s-cis) methyl-9-(1,3-dihydro-1,3-dioxo-2H-isoindol-2-yl)-3,4,7,8,9,10-hexahydro-6,10-dioxo-6H-pyridazino [1,2-a][1,2] diazepine-1-carboxylate.

The product of formula (I) of SS configuration in which R is a terbutyl radical and the amine is protected in the form of phthalimido, is described for example in the Patent EP 94095, this is an intermediate product in the synthesis of products having therapeutic properties.

The products of formula (I) generally can be used for the synthesis of medicaments as indicated in the above patent.

The following examples illustrate the invention without limiting it.

EXAMPLE 1

(1S-cis)Methyl-9-(1,3-dihydro-1,3-dioxo-2H-isoindol-2-yl)octahydro-6,10-dioxo-6H-pyridazino [1,2-a][1,2]diazepine-1-carboxylate and Methyl (1R-Trans)-9-(1,3-dihydro-1,3-dioxo-2H-isoindol-2-yl)octahydro-6,10-dioxo-6H-pyridazino [1,2-a) [1,2]diazepine-1-carboxylate.

a) Preparation of 2,5-Dibromopentanoic Acid 39 ml of bromine is added to a mixture of 106 g of 5-bromo pentanoic acid and 1 ml of phosphorus tribromide. The reaction mixture is taken to 70–80° C. for 16 hours 30 minutes. The reaction medium is taken to 100° C. for 15 minutes, then allowed to return to ambient temperature. 147 g of sought product is obtained.

b) Preparation of Ethyl 2,5-Dibromopentanoate 24.37 g of oxalyl chloride is added to a mixture containing 50 g of the product prepared in the preceding stage, 15 drops of DMF, and 300 ml of methylene chloride. The reaction mixture is maintained under agitation, at ambient temperature, until the reaction is complete. The reaction mixture is cooled down to 10° C. and 50 ml of ethyl alcohol is added. The reaction medium is agitated for 30 minutes at 10° C., left to return to ambient temperature and agitated for 3 hours at ambient temperature. After bringing to dryness, the sought product is obtained.

c) Preparation of Bis(phenylmethyl)1,2-hydrazinedicarboxylate 1.5 litres of methanol and 2s g of hydrazine monohydrate at 80% are placed under nitrogen. The reaction medium is cooled down to 0° C. and 75 g of benzyl chloroformate is introduced at 0° C., then another 75 g of benzyl chloroformate is introduced at the same time as a solution of 93 g of sodium carbonate in 1100 ml of demineralized water. The reaction mixture is maintained at 0° C. for 1 hour, followed by separating and washing by displacement with a mixture of 100 ml of methanol and 100 ml of water, then washing by displacement with 500 ml of water at 0° C. After drying, 107.6 g of sought product is obtained.

d) Preparation of (S) 3-Ethyl-1,2-bis(phenylmethyl)-tetrahydro-1,2,3-pyridazinetricarboxylate and (R) 3-Ethyl-1,2-bis(phenylmethyl)-tetrahydro-1,2,3-pyridazinetricarboxylate A suspension of 12.1 g of the product of ethyl 2,5-dibromopentanoate and 50 cm³ of diglyme is introduced at 20–25° C. into a suspension containing 10.42 g of bis (phenylmethyl) 1,2-hydrazinedicarboxylate, 65 ml of diglyme and 8.26 g of potassium carbonate.

The suspension obtained is heated at 90° C. Agitation is maintained for 48 hours, followed by cooling down to 20° C., pouring into a solution containing 50 ml of 2N hydrochloric acid and 150 ml of a mixture of water and ice, extracting with ethyl acetate, washing with water, drying, filtering, rinsing with ethyl acetate and drying. The product obtained is chromatographed on silica (elution heptane 40, AcOEt 20) and 10.71 g of sought product is obtained.

e) Preparation of (S) 1-(Phenylmethyl)-tetrahydro-1,3(2H)-pyridazinedicarboxylate and (R) 1-(Phenylmethyl)-tetrahydro-1,3(2H)-pyridazinedicarboxylate A solution containing 23.25 g of the product of the previous stage and 80 ml of ethanol is introduced into 338 ml of a solution of sodium hydroxide in ethanol at 40 g per litre. Agitation is maintained for 5 hours 30 minutes and 57 ml of 2N soda is added. The reaction mixture is maintained under agitation for 30 hours. 141 ml of a solution of 2N hydrochloric acid is added. 260 ml of the reaction mixture is distilled under 80~90 millibars. Extraction is carried out with dichloromethane, 20 ml of ethanol is added, followed by washing with a mixture of water-normal solution of soda The aqueous phases are extracted with dichloromethane. The aqueous phases are combined, agitated and acidified with 135 ml of a 2N solution of hydrochloric acid. Extraction is carried out with dichloromethane, followed by washing with water, drying, filtering, washing with methylene chloride, concentrating and drying. 146 ml of isopropyl ether is added, followed by agitation for 1 hour at 20° C., filtering, washing, concentrating and drying. 11.41 g of sought product is obtained.

f) Preparation of (S) 3-Methyl 1-(Phenylmethyl)tetrahydro-1,3(2H)-pyridazinedicarboxylate and (R) 3-Methyl 1-(Phenylmethyl)tetrahydro-1,3(2H)-pyridazinedicarboxylate 220 ml of methanol and dehydrated paratoluene sulphonic acid (prepared from monohydrated PTSA and 12 ml of dichioromethane) are added to 11.05 g of the product prepared in the previous stage. The suspension obtained is maintained under agitation for 15 hours, heated to 65° C. and maintained under agitation for 6 hours 30 minutes. After cooling down to 5° C., 5.5 ml of a 10% solution of sodium bicarbonate is added, followed by concentrating under reduced pressure, taking up in a mixture of 100 ml of dichloromethane and 100 ml of water. Agitation is carried out, followed by decanting, washing the organic phase, extracting with dichloromethane, drying, filtering and concentrating. 11.39 g of sought product is obtained.

g) Preparation of [3S-[2(R*),3R*]]3-Methyl 1-(Phenylmethyl) 2-[2-(1,3-dihydro-1,3-dioxo-2H-isoindol-2-yl)-1,5-dioxo-5-(phenylmethoxy)pentyl]tetrahydro-1,3 (2H)pyridazine Dicarboxylate and [3R-[2(S*),3R*]]3-Methyl 1-(Phenylmethyl) 2-[2-(1,3-Dihydro-1,3-dioxo-2H-isoindol-2-yl)-1,5-dioxo-5-(phenylmethoxy) pentyl]Tetrahydro-1,3(2H)pyridazine Dicarboxylate A solution containing 11.01 g of the product prepared in the previous stage and 50 ml of dichloromethane is introduced over 1 hour at about 4° C. into a solution containing 19.88 g of phenylmethyl (S)-gamma-(chlorocarbonyl)-1,3-dihydro-1,3-dioxo-2H-isoindole-2-butanoate and 100 ml of dichloromethane. Agitation is carried out for 30 minutes at 4° C. and 4.15 ml of pyridine in 25 ml of dichloromethane is introduced over 1 hour 30 minutes. Agitation is maintained for 15 hours while slowly allowing the reaction medium to return to ambient temperature, followed by concentrating under reduced pressure, taking up in 200 ml of ethyl acetate, washing with a saturated solution of sodium acid carbonate, agitating for 30 minutes, decanting, washing with a saturated solution of sodium acid carbonate, agitating and decanting. The reaction medium is washed with a solution containing 5 ml of a normal solution of hydrochloric acid and 25 ml of water, then with a saturated aqueous solution of sodium chloride and dried. Extraction is carried out with ethyl acetate, followed by concentrating and drying. 25.2 g of sought product is obtained.

h) Preparation of [6S-[(1(R*),6R*[]-1,3-Dihydro-1,3-dioxo-gamma-[[6-(methoxycarbonyl)-tetrahydro-1(2H)-pyridazinyl]carbonyl]-2H-isoindole-2-butanoic Acid and [6R-[(1(S*),6R*]]-1,3-Dihydro-1,3-dioxo-gamma-[[6-(methoxycarbonyl)-tetrahydro-1(2H)-pyridazinyl] carbonyl]-2H-isoindole-2-butanoic Acid 20.23 g of the product of the previous stage, 250 ml of THF and 3.03 g of palladium at 10% on carbon are introduced into a hydrogen apparatus. Hydrogen is passed through for 3 hours, another 3.03 g of catalyst is added. Hydrogenation is continued for 22 hours, followed by filtering, washing with THF and evaporating. 25 ml of isopropanol is added, followed by concentrating, driving off the THF, 15 ml of isopropanol is added. A suspension is obtained to which 100 ml of isopropyl ether is added, followed by agitation under nitrogen for 2 hours, separating, washing with isopropyl ether with 5% isopropanol. After separating and drying, 9.5 g of sought product is obtained.

I) Preparation of (1S-cis)Methyl-9-(1,3-dihydro-1,3-dioxo-2H-isoindol-2-yl)octahydro-6,10-dioxo-6H-pyridazino{1,2-a][1,2]diazepine-1-carboxylate and (1R-Trans)methyl-9-(1,3-dihydro-1,3-dioxo-2H-isoindol-2-yl)octahydro-6,10-dioxo-6H-pyridazino{1,2-a][1,2]diazepine-1-carboxylate A solution containing 1 ml of thionyl chloride and 40 ml of methylene chloride is added at 5° C. to a mixture containing 4.038 g of the product of the previous stage, 40 ml of dichloromethane and 0.4 ml of dimethylformamide. Agitation is carried out for 3 hours and 30 minutes. The temperature is left to rise towards 20° C., followed by agitation for one hour 30 minutes and concentrating. A solution containing 0.15 ml of thionyl chloride and 5 ml of methylene chloride is added. The reaction mixture is maintained under agitation at about 20° C. for 16 hours, followed by cooling down to about 5° C. and 27 ml of a saturated aqueous solution of sodium acid carbonate is introduced. Agitation is carried out for 30 minutes, followed by decanting and washing with a solution containing 10 ml of sodium bicarbonate and 40 ml of demineralized water. Agitation is carried out 3 minutes, followed by decanting, extracting the aqueous phases with methylene chloride, drying, filtering, washing with methylene chloride and concentrating under reduced pressure. 3.85 g of sought product is obtained.

Use of (1S-cis)Methyl-9-(1,3-dihydro-1,3-dioxo-2H-isoindol-2-yl)octahydro-6,10-dioxo-6H-pyridazino{1,2-a][1,2]diazepine-1-carboxylate A solution containing 0.029 g of potassium terbutylate and 0.3 ml of DMF is introduced at a temperature of −45°/−48° C. over 1 hour 30 minutes into a mixture containing 0.194 g of the product of Example 1, 1.5 ml of dimethylformamide and 0.75 ml of terbutanol. The mixture is maintained under agitation for 1 hour and after cooling down to −50° C., 0.4 g of powdered ammonium chloride is introduced. Agitation is carried out for 10 minutes at −45° C., 1 ml of ammonium chloride at 20% is added successively twice whilst agitating again for 10 minutes after each addition. 2 ml of demineralized water is added, followed by extracting with ethyl acetate, washing with demineralized water, decanting, concentrating and drying. 0.166 g of product is obtained. $\alpha_D$=−75.3° (1% in methanol)

What is claimed is:

1. A process for the preparation of a compound of the formula

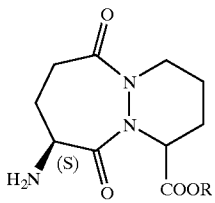

I of SR configuration or a SR+SS mixture wherein R is selected from the group consisting of hydrogen, alkyl of up to 18 carbon atoms and aryl and aralkyl of up to 18 carbon atoms and the —$NH_2$ is free or protected, comprising reacting a compound of the formula

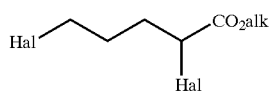

(II)

where Hal is halogen and alk is a alkyl of 1 to 8 carbon atoms with a compound of the formula

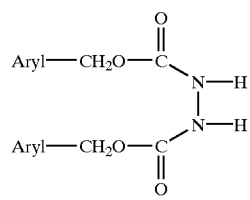

(III)

when Aryl is a aryl of up to 14 carbon atoms to form a compound of the formula

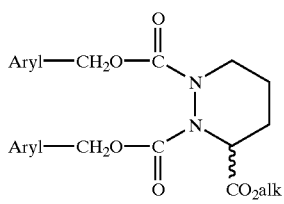

(IV)

reacting the latter with a basic agent to form a compound of the formula

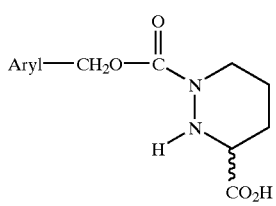

(V)

optionally subjecting the compound of Formula IV to an alkylating agent to form a compound of the formula

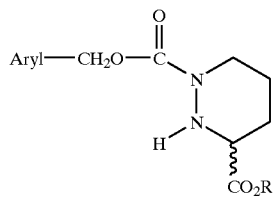

(VI)

reacting the latter with a compound of the formula

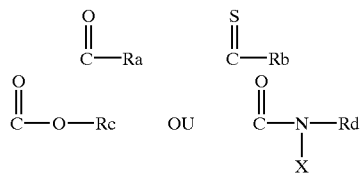

(VII)

wherein $Hal_1$ is halogen, Ar is aryl or aralkyl of up to 18 carbon atoms, $R_1$ is selected from the group consisting of $$\underset{}{\overset{O}{\underset{\|}{C}}}-R_a \qquad \underset{}{\overset{S}{\underset{\|}{C}}}-R_b$$

$$\underset{}{\overset{O}{\underset{\|}{C}}}-O-R_c \quad OU \quad \underset{X}{\overset{O}{\underset{\|}{C}}}-N-R_d$$

$R_a$, $R_b$, $R_c$ and $R_d$ are individually selected from the group consisting of alkyl of up to 18 carbon atoms, aryl of up to 18 carbon atoms and monocyclic and polycyclic groups containing at least one nitrogen atom, X is selected from the group consisting of hydrogen, alkyl of 1 to 8 carbon atoms and aryl of up to 14 carbon atoms and $R_2$ is hydrogen or $R_1$ and $R_2$ together with the nitrogen form a monocyclic or polycyclic with at least one heteroatom to obtain a compound of the formula

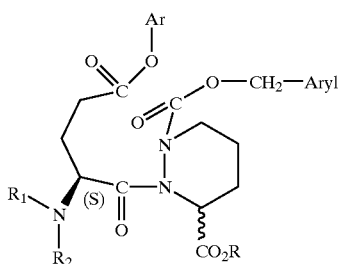

(VIII)

of SR configuration on a SR+SS mixture, reacting the latter with a hydrogenation agent to form a compound of the formula

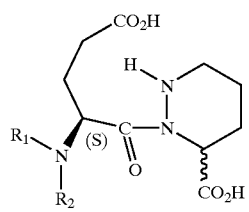

of SR configuration or a SR+SS mixture, reacting the latter with a condensation agent to obtain a compound of the formula

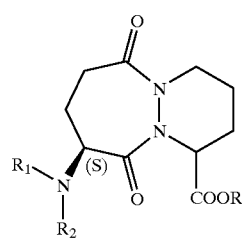

and optionally deprotecting the amine group to obtain a compound of formula I wherein the amine is free.

2. A process for the preparation of a compound of the formula

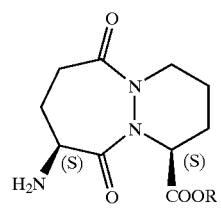

comprising reacting a compound of the formula

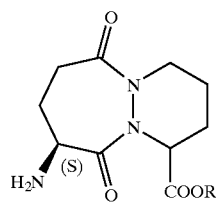

of SR configuration or a SR+SS mixture wherein R is selected from the group consisting of hydrogen, alkyl of up to 18 carbon atoms and aryl and aralkyl of up to 18 carbon atoms and the —$NH_2$ is free or protected, with a deracemization agent of the asymmetric carbon carried by the 6-member ring to obtain the formula Iopt in SS form with the amine free or protected.

3. A process for the preparation of a compound of the formula

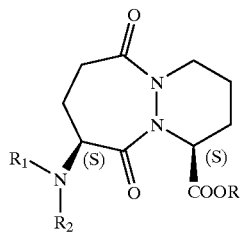

comprising reacting a compound of of the formula

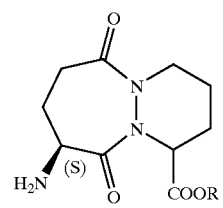

of SR configuration or a SR+SS mixture wherein R is selected from the group consisting of hydrogen, alkyl of up to 18 carbon atoms and aryl and aralkyl of up to 18 carbon atoms and the —$NH_2$ is free or protected, with a deracemization agent of the asymmetric carbon carried by the 6-member ring to obtain the formula Iopt in SS form with the amine free or protected.

4. The process of claim 2 wherein R is methyl.

5. The process of claim 2 wherein the —$NH_2$ is protected by phthalimido.

6. The process of claim 2 wherein the deracemization agent is a base.

7. The process of claim 6 wherein the base is selected from the group consisting of an alkali metal alcoholate, an alkaline earth metal alcoholate and a lithiated amine.

8. The process of claim 3 wherein the final product is (is-cis) methyl-9-(1,3-dihydro-1,3-dioxo-2H-isoindol-2-yl)-3,4,7,8,9,10-hexahydro-6,10-dioxo-6H-pyridazino [1,2-a][1,2]-diazepine-1-methyl-carboxylate.

* * * * *